(12) United States Patent
Mainardi et al.

(10) Patent No.: US 8,258,127 B2
(45) Date of Patent: Sep. 4, 2012

(54) METHODS FOR TREATING LATENT TUBERCULOSIS

(75) Inventors: Jean-Luc Mainardi, Chaville (FR); Michel Arthur, Arcuell (FR); Laurent Gutmann, Paris (FR); Marie Lavollay, Bourg la Reine (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 107 days.

(21) Appl. No.: 12/180,802

(22) Filed: Jul. 28, 2008

(65) Prior Publication Data

US 2010/0022504 A1    Jan. 28, 2010

(51) Int. Cl.
*A61K 31/407* (2006.01)
*A61K 31/00* (2006.01)

(52) U.S. Cl. ........... 514/210.09; 514/210.05; 514/210.1; 514/210.12

(58) Field of Classification Search ......................... None
See application file for complete search history.

(56) References Cited

OTHER PUBLICATIONS

Chambers et al., "Imipenem for Treatment of Tuberculosis in Mice and Humans," Antimicrobial Agents and Chemotherapy, Jul. 2005; 49(7): pp. 2816-2821.*
Blumberg et al., "Update on the Treatment of Tuberculosis and Latent Tuberculosis Infection," JAMA, 2005; 293(22): pp. 2776-2784.*
Lavollay et al., Journal of Bacteriology, 2008, 190:4360.*
Manabe and Bishai, "Latent *Mycobacterium tuberculosis*-persistence, patience, and winning by waiting," Nature Medicine, 2000, 6: pp. 1327-1329.*
Wayne and Hayes, "An In Vitro Model for Sequential Study of Shiftdown of *Mycobacterium tuberculosis* through Two Stages of Nonreplicated Persistence," Infection and Immunity, Jun. 1996, pp. 2062-2069.*
Connolly et al. "Why is Long-Term Therapy Required to Cure Tuberculosis'?," PLoS Medicine, 2007, 4 e120: pp. 0435-0042).*

* cited by examiner

*Primary Examiner* — Sreeni Padmanabhan
*Assistant Examiner* — Jody Karol
(74) *Attorney, Agent, or Firm* — Young & Thompson

(57) ABSTRACT

A method for treating individuals affected with latent tuberculosis comprising a step of administering an effective amount of one or more carbapenem compounds to the said individuals.

4 Claims, 10 Drawing Sheets

B

A

METHODS FOR TREATING LATENT TUBERCULOSIS

FIELD OF THE INVENTION

Figure 1:
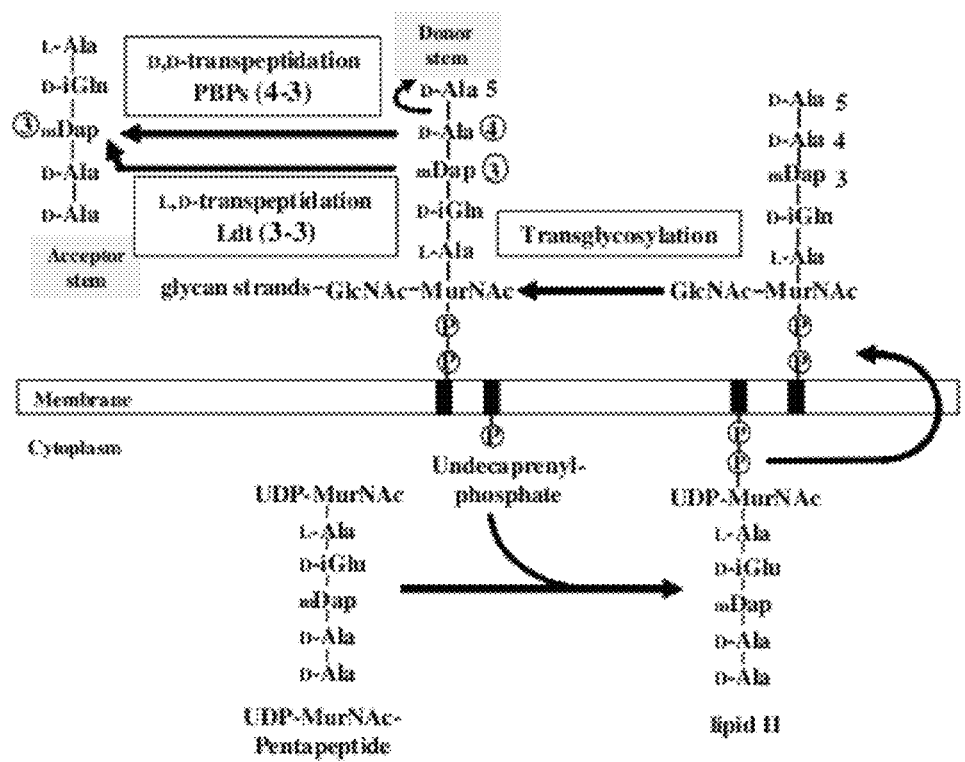

The present invention relates to the field of anti-microbial therapy, and more precisely to methods for the screening of antibacterial substances active against *Mycobacterium tuberculosis*, especially against *Mycobacterium tuberculosis* in a stationary state.

The present invention also relates to therapeutic methods against latent tuberculosis.

BACKGROUND OF THE INVENTION

In spite of a stable decline in the incidence of tuberculosis in countries participating to control surveys, there were an estimated 8.8 millions new cases and 1.6 million deaths in 2005. In fact, numbers of individuals succumbing to tuberculosis have vastly increased as a result of the HIV/AIDS pandemic, and increased mobility owing to global travel has increased the transfer of virulent and multidrug-resistant tuberculosis. Compared with other infections there are relatively few antimicrobial agents that are clinically active against *Mycobacterium tuberculosis*. Prolonged antibiotic treatment is also required, as the bacterium can enter a dormant, antibiotic-resistant phase.

Except for very young children, few people that have been infected with *Mycobacterium tuberculosis* become sick immediately after tuberculosis bacteria enter in their body (primary infection). Many tuberculosis bacteria that enter the lungs are immediately killed by the body's defences. The bacteria cells that survive are captured inside macrophages. The captured bacteria can remain alive inside these cells in a dormant state for many years, walled off inside tiny scars (latent infection). In 90 to 95% of cases, the bacteria never cause any further symptom. Nevertheless, in about 5 to 10% of infected people bacteria cells start to multiply and these people actually enter into the symptomatic disease state. It is in this active phase of the tuberculosis disease that an infected person actually becomes sick and can spread the disease.

Infection with *Mycobacterium tuberculosis* usually results in so-called primary tuberculosis or Ghon's complex in approximately 90% of the individuals. This usually limited infection comprises a focal multiplication of the *Mycobacterium* in the lung tissue in association with lymphangitis, infection, and massive enlargement of the corresponding hilar draining lymph node. In approximately 95% of these individuals, the inflammatory reaction is spontaneously contained and in many cases calcifies and persists for the remainder of the person's life.

In more than half of the infected individuals, activation of dormant bacteria happens within the first 2 years following the time of infection, but this activation may not occur for a very long time, in some cases for up to 5 years following the time of infection. Activation of dormant *M. tuberculosis* bacterium cells often occurs when the individual's immune system becomes impaired—for example, from very advanced age, the use of corticosteroids, or AIDS. Like many infectious diseases, tuberculosis spreads more quickly and is much more dangerous in people who have a weakened immune system. For such people (including the very young, the very old, and those who are also infected with HIV), tuberculosis can be life threatening.

Thus, notwithstanding the clinical resolution of Ghon's complex, several *M. tuberculosis* organisms remain viable for life, a condition known as latent or dormant tuberculosis.

Primary tuberculosis usually stimulates strong and long-lasting cellular immune response to *M. tuberculosis* antigens, which can be detected even years later by the delayed-type hypersensitivity skin test (the purified protein derivative [PPD] or Mantoux test). Reactivation of latent tuberculosis leading to chronic pulmonary tuberculosis or adult tuberculosis may occur afterwards, even decades later, due to intervening events such as malnutrition or immunosuppression. However, clinical and molecular evidence indicates that adult tuberculosis occurs most often due to exogenous reinfection with *M. tuberculosis* in geographical areas where the rate of contagion is high, such as in many developing countries. Although the general consensus is that adult tuberculosis caused by reactivation of latent infection is associated with some predisposing immunodeficiency, the need for such an intervening condition for disease development due to exogenous reinfection of PPD-positive healthy immunocompetent individuals is still a controversial issue. Unfortunately, experiments designed to study this controversy have been hampered by the lack of a reliable animal model of dormant infection. Moreover, such an animal model is in high demand for validation of vaccine candidates in the context of presensitization with *M. tuberculosis* antigens, a condition highly prevalent among the human population in need of an antituberculosis vaccine.

The treatment of *M. tuberculosis* infections requires at least six months of antimycobacterial therapy with the association of multiple drugs. This long duration of treatment is justified by the poor efficacy of available antibiotics, including the main drugs isoniazid and rifampin, against dormant *M. tuberculosis* bacilli that are thought to persist in particular environment such as granuloma or caseum. In vitro models that mimic the persistent state have been developed based on nutrient starvation, oxygen deprivation and exposure to nitric oxide. These models showed that non-replicative and low metabolic states of the bacteria could be responsible for the poor in vivo response to currently available drugs.

There is thus a need in the art for novel antibacterial substances for treating infection of individuals with *Mycobacterium tuberculosis*. Importantly, there is a need in the art for novel compounds that are active against the dormant state of *M. tuberculosis*, so as to prevent activation of the bacteria cells in the infected individuals, especially in immuno-compromised individuals for whom entering into the clinical phase of tuberculosis would be life-threatening.

Several attempts have already performed in the art for identifying antibacterial substances having bactericidal properties against *Mycobacterium tuberculosis* cells in the dormant state.

Notably, Hu et al. have disclosed the in vitro bactericidal activity of pyrazinamide, a sterilizing substance, against *M tuberculosis* cells cultivated in starvation conditions mimicking cells in dormant state (Hu et al., 2006, International Journal of tuberculosis and lung disease, Vol. 10(no3): 317-322). These authors have shown that pyrazinamide possess an increased bactericidal activity towards *M tuberculosis* bacteria with low metabolic activity, as compared with normal bacterial cells.

Also, Murphy et al. have taken benefit from genome-wide *M tuberculosis* gene expression data for identifying several genes that were found up- or down-regulated specifically in bacterial cells under simulated dormancy conditions (Murphy et al., 2007, BMC Infectious diseases, Vol. 7: 84). These authors have determined that promising targets for drug discovery included several regulatory elements (devR/devS, relA, mprAB) enzymes involved in redox balance and respiration, sulfur transport and fixation, pantothenate, isoprene and NAD biosynthesis.

However, there is still a need for novel *M tuberculosis* bactericidal substances, especially substances which are active against the dormant state of *M tuberculosis* bacteria cells, as well as to methods for the screening such bactericidal substances.

SUMMARY OF THE INVENTION

The present invention relates to a method for the screening of antibacterial substances comprising a step of determining the ability of a candidate substance to inhibit the activity of a purified L,D-transpeptidase enzyme from *Mycobacterium tuberculosis* having at least 90% amino acid sequence identity with the amino acid sequence of SEQ ID No 1, or a biologically active fragment thereof This invention also deals with a method for the screening of antibacterial substances which comprises the steps of:

a) providing a composition comprising the said purified L,D-transpeptidase enzyme or the said biologically active fragment thereof, and a substrate thereof;
b) adding the candidate substance to be tested to the composition provided at step a), whereby providing a test composition; and
c) comparing the activity of the said L,D-transpeptidase enzyme in the said test composition with the activity of the said L,D-transpeptidase enzyme in the absence of the said candidate substance;
d) selecting positively the said candidate substance that inhibits the catalytic activity of the said L,D-transpeptidase enzyme.

This invention also pertains to a method for the screening of antibacterial substances comprising the steps of:

a) providing a candidate substance;
b) assaying the said candidate substance for its ability to bind to a L,D-transpeptidase enzyme from *Mycobacterium tuberculosis* having at least 90% amino acid sequence identity with the amino acid sequence of SEQ ID No 1, or to a biologically active fragment thereof.

This invention also concerns a kit for the screening of an antibacterial substance comprising a purified L,D-transpeptidase enzyme from *M. tuberculosis* having at least 90% amino acid sequence identity with the amino acid sequence of SEQ ID No 1, or a biologically active fragment thereof.

This invention also pertains to the use of carbapenems for manufacturing pharmaceutical compositions for treating individuals infected by *Mycobacterium tuberculosis* undergoing an asymptomatic phase of the disease.

BRIEF DESCRIPTION OF THE DRAWINGS

FIG. 1 illustrates a schematic representation of peptidoglycan synthesis. The nucleotide UDP-MurNAc-pentapeptide is formed in the cytoplasm by sequential addition of L-Ala, D-Glu, meso-diaminopimelic acid (mDap), and of the dipeptide D-Ala-D-Ala. The membrane steps of peptidoglycan synthesis involve the transfer of the phospho-MurNAc-pentapeptide moiety of the nucleotide to the lipid carrier (undecaprenyl-phosphate) and the addition of the second sugar (GlcNAc). The complete precursor linked to the lipid carrier (lipid II) is translocated through the membrane and polymerized by glycosyltransferases (formation of glycan strands) and by the D,D-transpeptidase activity of penicillin-binding proteins (PBPs) (formation of the cross-links). These enzymes cleave the D-Ala4-D-Ala5 bond of a pentapeptide donor and link the carbonyl of D-Ala4 to the side chain amine of mDap at the third position of an acceptor stem (4-3 cross-links). Beta-Lactam antibiotics are structural analogues of the D-Ala4-D-Ala5 extremity of the precursors and act as suicide substrates of the D,D-transpeptidases. L,D-transpeptidases cleave the mDap3-D-Ala4 bond of a tetrapeptide donor and link the carbonyl of mDap3 to the acceptor stem (3-3 cross-links).

FIG. 2A to 2D together show the structure of the peptidoglycan of *M. tuberculosis.*

FIG. 2A: Rp-HPLC profile of peptidoglycan fragments obtained by digestion of the peptidoglycan of strain H37Rv with muramidases and treatment with ammonium hydroxide. mAU, absorbance unit×$10^3$ at 210 nm.

FIG. 2B: Structure of monomers. D-iGln, D-iso-glutamine; D-iGlu, D-iso-glutamic acid; D-Lac: D-lactate; GlcNAc-MurNGlyc$^{anh}$; N-acetylglucosamine-anhydro-N-glycolylmuramic acid; mDap: meso-diaminopimelic acid; mDaP$_{NH2}$: mDap with an amidated ε carboxyl group.

FIG. 2C: Sequencing of a dimer generated by L,D-transpeptidation. Tandem mass spectrometry was performed on the $[M+H]^+$ ion at m/z 974.6 (peak 10). Boxes indicate ions generated by cleavage at single peptide bounds.

FIG. 2D: Sequencing of a dimer generated by D,D-transpeptidation (peak 13; $[M+H]^+$ ion at m/z 1,045.4).

FIG. 3A: illustrates the characterization of Ldt$_{Mt1}$ from *M. tuberculosis.*

FIG. 3B: Purification of a soluble fragment of Ldt$_{Mt1}$ produced in *E. coli.*

FIG. 3C: Analysis of a dimer formed in vitro by Ldt$_{Mt1}$. Fragmentation was performed on the $[M+H]^+$ ion at m/z 974.5. Boxes indicate ions generated by cleavage at single peptide bonds.

FIG. 3D: Structure of the dimer and inferred fragmentation pattern.

FIG. 4 illustrates the formation of adducts between Ldt$_{Mt1}$ and β-lactams.

Ldt$_{Mt1}$ (12.5 μM) was incubated without antibiotic (left panel) or with 125 μM imipenem (right panel). Proteins and adducts were detected by electrospray mass spectrometry. Peaks at m/z 848.75 and 879.03 correspond to the $[M+29H]^{29+}$ and $[M+28H]^{28+}$ ions of the native protein, respectively (deduced average mass of 24,584.4). Peaks at m/z 859.08 and 889.65 correspond to the $[M+29H]^{29+}$ and $[M+28H]^{28+}$ ions of the Ldt$_{Mt1}$-imipenem adduct (deduced average mass of 24,883.5).

DETAILED DESCRIPTION OF THE INVENTION

It has been surprisingly found according to the invention that, in the peptidoglycan structure of *Mycobacterium tuberculosis* cells in the dormant state, cross-linking of the glycan strands is very specific.

More precisely, it has been shown according to the invention that the peptidoglycan network from *M tuberculosis* cells in dormant state mainly comprises 3→3 cross-links. Still more precisely, it as been found according to the invention that the peptidoglycan network from *M tuberculosis* cells in dormant state comprises up to more than 80% of 3→3 cross-links.

A schematic representation of *Mycobacterium tuberculosis* peptidoglycan including the 3→3 cross-links as determined by the inventors is presented in FIG. 1.

It has further been surprisingly shown according to the invention that *M tuberculosis* cells in dormant state specifically express a transpeptidase with L,D specificity. It is shown herein that the said L,D-transpeptidase, which has been termed "Ldt$_{Mt1}$", effectively catalyzes the generation of 3→3 cross-links between glycan molecules.

Thus, it has been found according to the invention that the Ldt$_{Mt1}$ L,D-transpeptidase, which is specifically expressed in *M tuberculosis* cells in dormant state consists of a highly valuable target protein for substances that will inhibit or block the activity of the said enzyme and thus for substances having antibacterial properties against *M. tuberculosis* cells, especially in dormant state.

An object of the present invention consists of a method for the screening of antibacterial substances comprising a step of determining the ability of a candidate substance to inhibit the activity of a purified L,D-transpeptidase enzyme from *Mycobacterium tuberculosis* having at least 90% amino acid sequence identity with the amino acid sequence of SEQ ID No 1, or a biologically active fragment thereof.

As shown in the examples herein, the screening method above has been successfully used for selecting positively candidate substances. It is shown herein that carbapenems, including imipenem, meropenem and ertapenem block the said L,D-transpeptidase enzyme, whereas other antibiotics like ampicillin is inactive. Regarding the carbapenem compounds that have been assayed, formation of adducts with the said L,D-transpeptidase have been determined, which shows an irreversible blocking of this enzyme.

As intended herein, a "L,D-transpeptidase" encompasses a polypeptide comprising an amino acid sequence having at least 90% amino acid identity with the amino acid sequence of SEQ ID No 1, as well as any biologically active fragment thereof.

The amino acid sequence of SEQ ID No 1 consists of the amino acid sequence of the $Ldt_{Mt1}$ L,D-transpeptidase which is expressed in *M tuberculosis* cells in dormant state.

It has been shown in the examples herein that fragments of the $Ldt_{Mt1}$ L,D-transpeptidase are biologically active, such as the $Ldt_{Mt1}$-derived polypeptide having the amino acid sequence starting at the prolyl residue located at position 32 of SEQ ID No 1 and ending at the glycyl residue located at position 251 of SEQ ID No 1.

It is herein also expected that any polypeptide having 90% amino acid identity with the polypeptide comprising the amino acid sequence beginning at the glycyl residue located at position 121 and ending at the valyl amino acid residue located at position 249 of SEQ ID No 1 consists of a biologically active fragment of the L,D-transpeptidase of SEQ ID No 1.

Thus, according to preferred embodiments, a biologically active fragment of a L,D-transpeptidase of the invention possesses at least 90% amino acid identity with the amino acid sequence beginning at the glycyl residue located at position 121 and ending at the valyl amino acid residue located at position 249 of SEQ ID No 1 consists of a biologically active fragment of the L,D-transpeptidase of SEQ ID No 1.

Generally, a biologically active fragment of $Ldt_{Mt1}$ L,D-transpeptidase according to the invention has an amino acid length of at least 129 amino acid residues. Usually, a biologically active fragment of $Ldt_{Mt1}$ L,D-transpeptidase according to the invention comprises at least 129 consecutive amino acid residues of $Ldt_{Mt1}$ L,D-transpeptidase of SEQ ID No 1.

Those biologically active peptide fragments encompassed herein include those having 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199; 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251 consecutive amino acids of SEQ ID No 1 and comprising the amino acid sequence beginning at the glycyl residue located at position 121 and ending at the valyl amino acid residue located at position 249 of SEQ ID No 1

As intended herein, LdtMt1 L,D-transpeptidase according to the invention, or any biologically active peptide thereof, "comprises" a polypeptide as defined above because, in certain embodiments, said L,D-transpeptidase may not simply consist of the polypeptide defined above. Illustratively, the $Ldt_{Mt1}$ L,D-transpeptidase according to the invention, or any biologically active peptide thereof, may comprise, in addition to a polypeptide as defined above, additional amino acid residues that are located (i) at the N-terminal end, (ii) at the C-terminal end or (iii) both at the N-terminal end and at the C-terminal end of said polypeptide above. Generally, at the N-terminal end or at the C-terminal end of a polypeptide defined above, there is no more than 30 additional amino acid residues and often no more than 29, 28, 27, 26, 25, 24, 23, 22, 21, 20, 19, 18, 17, 16, 15, 14, 13, 12, 11, 10, 9, 8, 7, 6, 5 or 4 additional amino acid residues. Illustratively, a polypeptide as defined above that possesses a L,D-transpeptidase activity possesses, at its C-terminal end, six additional Histidine amino acid residues.

As intended herein, a polypeptide or a protein having at least 90% amino acid identity with a reference amino acid sequence possesses at least 90%, 91%, 92%, 93%, 94%, 95%, 96%, 97%, 98%, 99% or 99.5% amino acid identity with the said reference amino acid sequence.

For the purpose of determining the percent of identity of two amino acid sequences according to the present invention, the sequences are aligned for optimal comparison purposes. For example, gaps can be introduced in one or both of a first and a second amino acid sequence for optimal alignment and non-homologous sequences can be disregarded for comparison purposes.

For optimal comparison purposes, the percent of identity of two amino acid sequences can be achieved with CLUSTAL W (version 1.82) with the following parameters: (1) CPU MODE=ClustalW mp; (2) ALIGNMENT=<<full>>; (3) OUTPUT FORMAT=<<aln w/numbers>>; (4) OUTPUT ORDER=<<aligned>>; (5) COLOR ALIGNMENT=<<no>>; (6) KTUP (word size)=<<default>>; (7) WINDOW LENGTH=<<default>>; (8) SCORE TYPE=<<percent>>; (9) TOPDIAG=<<default>>; (10) PAIRGAP=<<default>>; (11) PHYLOGENETIC TREE/TREE TYPE=<<none>>; (12) MATRIX=<<default>>; (13) GAP OPEN=<<default>>; (14) END GAPS=<<default>>; (15) GAP EXTENSION=<<default>>; (16) GAP DISTANCES=<<default>>; (17) TREE TYPE=<<cladogram>> et (18) TREE GRAP DISTANCES=<<hide>>.

By a "biologically active fragment" of the $Ldt_{Mt1}$ L,D-transpeptidase that is defined above, it is intended herein a polypeptide having an amino acid length that is shorter than the amino acid length of the enzyme polypeptide of reference, while preserving the same L,D-transpeptidase activity, that is the same specificity of catalytic activity and an activity of at least the same order of magnitude than the activity of the parent enzyme polypeptide.

A biologically active fragment of the $Ldt_{Mt1}$ L,D-transpeptidase according to the invention possesses a L,D-transpeptidase activity that may be assessed using, as the substrate, the disaccharide-tetrapeptide (GlcNac-MurNac-L-$Ala^1$-D- iGln²-mesoDap$_{NH2}$³-D-Ala⁴). A peptide fragment from the Ldt$_{Mt1}$ L,D-transpeptidase according to the invention consists of a biologically active fragment thereof if the rate of production of the final dimer product is of at least 0.1 the rate of Ldt$_{Mt1}$ L,D-transpeptidase of SEQ ID No 1.

In a preferred embodiment of the method for the screening of antibacterial substances that is defined above, said method comprises the steps of:
a) providing a composition comprising the said purified L,D-transpeptidase enzyme or the said biologically active fragment thereof, and a substrate thereof;
b) adding the candidate substance to be tested to the composition provided at step a), whereby providing a test composition; and
c) comparing the activity of the said L,D-transpeptidase enzyme in the said test composition with the activity of the said L,D-transpeptidase enzyme in the absence of the said candidate substance;
d) selecting positively the said candidate substance that inhibits the catalytic activity of the said L,D-transpeptidase enzyme.

As intended herein, a candidate substance to be tested inhibits the catalytic activity of the said L,D-transpeptidase if the activity of the said enzyme, when the candidate substance is present, is lower than when the said enzyme is used without the candidate substance under testing.

Preferably, the candidate substances that are positively selected at step d) of the method above are those that cause a decrease of the production rate of the final product by the said L,D-transpeptidase that leads to less than 0.5 times the production rate of the same enzyme in the absence of the candidate substance, more preferably a decrease that leads to less 0.3, 0.2, 0.1, 0.05 or 0.025 times the production rate of the same enzyme in the absence of the candidate substance. The most active candidate substances that may be positively selected at step d) of the method above may completely block the catalytic activity of said enzyme, which leads to a production rate of the final product by said L,D-transpeptidase which is undetectable, i.e. zero, or very close to zero.

In certain embodiments of the screening method above, said enzyme consists of a L,D-transpeptidase comprising a polypeptide having an amino acid sequence possessing at least 90% amino acid identity with the amino acid sequence of SEQ ID No 1, or a biologically active fragment thereof.

In still further embodiments of the screening method above, said enzyme consists of a L,D-transpeptidase comprising a polypeptide having the amino acid sequence of SEQ ID No 1, or a biologically active fragment thereof.

In yet further embodiments of the screening method above, the said L,D-transpeptidase enzyme consists of the polypeptide having the amino acid sequence of SEQ ID No 1, or a biologically active fragment thereof In preferred embodiments of the screening method above, the catalytic activity of the said L,D-transpeptidase enzyme is assessed using, as the substrate, the disaccharide-tetrapeptide (GlcNac-MurNac-L-Ala1-D-iGln2-mesoDapNH23-D-Ala4).

According to the preferred embodiments above, the catalytic activity of the said L,D-transpeptidase enzyme is determined by detecting or quantifying the formation of muropeptide dimers by crosslinking the disaccharide-tetrapeptide Illustratively, the disaccharide-tetrapeptide (GlcNac-MurNac-L-Ala1-D-iGln2-mesoDapNH23-D-Ala4) substrate may be obtained by purification from *C. jeikeium*, e.g. the publicly available strain of *C. jeikeium* that is referred to as CIP-103337 at the Collection from Institut Pasteur (Paris, France).

Illustratively, in vitro formation of muropeptide dimers may be performed in a reaction mixture consisting of a 50 mM Tris-HCl (pH 7.5) and 300 mM NaCl buffer solution comprising (i) the purified LdtMt1 L,D-transpeptidase at a final concentration of 11 μM and (ii) the disaccharide-tetrapeptide substrate at a final concentration of 280 μM. Then the reaction mixture above may be incubated for about 2 hours at 37° C. and then treated with ammonium hydroxide, so as to obtain the resulting crosslinked lactoyl peptides, the identity of which is then determines, e.g. by nanoelectrospray tandem mass spectrometry analysis, e.g. using $N_2$ as the collision gas.

Production of the Ldt$_{Mt1}$ L,D-Transpeptidase Having at Least 90% Amino Acid Identity with the Amino Acid Sequence of SEQ ID No 1, or a Biologically Active Fragment Thereof.

Preferably, the Ldt$_{Mt1}$ L,D-transpeptidase having at least 90% amino acid identity with the amino acid sequence of SEQ ID No 1, or a biologically active fragment thereof, is produced as a recombinant protein.

Illustratively, the nucleic acid sequence encoding the Ldt$_{Mt1}$ L,D-transpeptidase of SEQ ID No 1 may consist of the nucleic acid sequence of SEQ ID No 2.

For obtaining a recombinant form of the Ldt$_{Mt1}$ L,D-transpeptidase having at least 90% amino acid identity with the amino acid sequence of SEQ ID No 1, or a biologically active fragment thereof, the one skilled in the art may insert the nucleic acid encoding the corresponding polypeptide into a suitable expression vector and then transfect appropriate cells with the resulting recombinant vector. Methods of genetic engineering for producing the polypeptides having an L,D-transpeptidase activity according to the invention under the form of recombinant polypeptides are well known from the one skilled in the art.

As it is well known from the one skilled in the art, the recombinant vector preferably contains a nucleic acid that enables the vector to replicate in one or more selected host cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter operably linked to the nucleic acid sequence encoding the polypeptide of interest to direct mRNA synthesis. Promoters recognized by a variety of potential host cells are well known. Promoters suitable for use with prokaryotic hosts include the .beta.-lactamase and lactose promoter systems (Chang et al., Nature, 275: 615 (1978); Goeddel et al., Nature, 281: 544 (1979)), alkaline phosphatase, a tryptophan (trp) promoter system (Goeddel, Nucleic Acids Res., 8:4057 (1980); EP 36,776), and hybrid promoters such as the tac promoter (deBoer et al., Proc. Natl. Acad. Sci. USA, 80: 21-25 (1983)). promoters for use in bacterial systems also will contain a Shine-Dalgarno (S.D.) sequence operably linked to the DNA encoding the polypeptide of interest.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding polypeptide of interest.

As shown in the examples herein, the nucleic acid encoding the polypeptide of interest having an L,D-transpeptidase activity may be inserted into the expression vector pET2818 which was previously disclosed by Mainardi et al. (2007, J. Biol. Chem., Vol. 275: 16490-16496). In this specific embodiment, the resulting recombinant polypeptide consists of a polypeptide having an extra-methionine residue at its N-terminal end and a polyhistidine tag having the sequence GS[H]$_6$ at its C-terminal end.

Illustratively, a recombinant vector having inserted therein a nucleic acid encoding a polypeptide of interest according to the invention having an L,D-transpeptidase activity may be transfected to bacterial cells in view of the recombinant polypeptide production, e.g. *E. coli* cells as shown in the examples herein.

Then, the recombinant polypeptide of interest having an L,D-transpeptidase activity may be purified, e.g. by one or more chromatography steps, including chromatography steps selected from the group consisting of affinity chromatography, ion exchange chromatography and size exclusion chromatography.

Illustratively, the recombinant polypeptide of interest having an L,D-transpeptidase activity may be purified by performing a purification method comprises (a) a step of affinity chromatography, e.g. on a Ni2+-nitriloacetate-agarose resin, (b) a step of anion exchange chromatography with the eluate of step (a) and (c) a size exclusion chromatography with the eluate of step (b).

The purified recombinant polypeptide of interest having an L,D-transpeptidase activity may be subjected to a concentration step, e.g. by ultrafiltration, before being stored in an appropriate liquid solution, e;g. at a temperature of −20° C.

Alternatively, a recombinant polypeptide of interest having an L,D-transpeptidase activity may be produced by known methods of peptide synthesis. For instance, the polypeptide sequence of interest, or portions thereof, may be produced by direct peptide synthesis using solid-phase techniques. (See, e.g., Stewart et al., Solid-Phase Peptide Synthesis (W.H. Freeman Co.: San Francisco, Calif., 1969); Merrifield, J. Am. Chem. Soc., 85: 2149-2154, 1963). In vitro protein synthesis may be performed using manual techniques or by automation. Automated synthesis may be accomplished, for instance, with an Applied Biosystems Peptide Synthesizer (Foster City, Calif.) using manufacturer's instructions. Various portions of the polypeptide of interest may be chemically synthesized separately and combined using chemical or enzymatic methods to produce the full-length polypeptide of interest Other Embodiments of In Vitro Screening Methods According to the Invention.

As detailed previously in the specification, this invention encompasses methods for the screening of candidate antibacterial substances that inhibit the activity of a L,D-transpeptidase as defined herein.

However, this invention also encompasses methods for the screening of candidate antibacterial substances, that are based on the ability of said candidate substances to bind to a L,D-transpeptidase as defined herein, thus methods for the screening of potentially antibacterial substances The binding assays can be performed in a variety of formats, including protein-protein binding assays, biochemical screening assays, immunoassays, and cell-based assays, which are well characterized in the art.

All binding assays for the screening of candidate antibacterial substances are common in that they comprise a step of contacting the candidate substance with a L,D-transpeptidase as defined herein, under conditions and for a time sufficient to allow these two components to interact.

These screening methods also comprise a step of detecting the formation of complexes between said L,D-transpeptidase and said candidate antibacterial substances.

Thus, screening for antibacterial substances include the use of two partners, through measuring the binding between two partners, respectively (i) a L,D-transpeptidase as defined herein and (ii) the candidate compound.

In binding assays, the interaction is binding and the complex formed between a L,D-transpeptidase as defined above and the candidate substance that is tested can be isolated or detected in the reaction mixture. In a particular embodiment, (i) the L,D-transpeptidase as defined above, (ii) or alternatively the antibacterial candidate substance, is immobilized on a solid phase, e.g., on a microtiter plate, by covalent or non-covalent attachments. Non-covalent attachment generally is accomplished by coating the solid surface with a solution of the L,D-transpeptidase as defined above and drying. Alternatively, an immobilized antibody, e.g., a monoclonal antibody, specific for the L,D-transpeptidase as defined above to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

The binding of the antibacterial candidate substance to a L,D-transpeptidase as defined above may be performed through various assays, including traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340: 245-246 (1989); Chien et al., Proc. Natl. Acad. Sci. USA, 88: 9578-9582 (1991)) as disclosed by Chevray and Nathans, Proc. Natl. Acad. Sci. USA, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for .beta.-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Thus, another object of the invention consists of a method for the screening of antibacterial substances, wherein said method comprises the steps of:
a) providing a candidate substance;
b) assaying said candidate substance for its ability to bind to a L,D-transpeptidase as defined above;

The same method may also be defined as a method for the screening of antibacterial substances, wherein said method comprises the steps of:
a) contacting a candidate substance with a L,D-transpeptidase as defined herein, or with a biologically active fragment thereof;
b) detecting the complexes eventually formed between (i) said L,D-transpeptidase as defined herein, or with said biologically active fragment thereof and (ii) said candidate substance.

The candidate substances, which may be screened according to the screening method above, may be of any kind, including, without being limited to, natural or synthetic compounds or molecules of biological origin such as polypeptides.

Binding Assays Based on Enzyme Peptide Mapping

According to one embodiment of the screening method above, step b) comprises a step of proteolysis of said L,D-transpeptidase prior to the detection of a binding between the candidate inhibitor substance and said enzyme.

More precisely, according to this specific embodiment of step b) of the screening method described above, said L,D-transpeptidase is incubated with a protease during a time period sufficient to generate a plurality of peptide fragments. Then, a step of detection of formation of eventual complexes between at least one of these peptide fragments and the candidate inhibitor compound is performed.

According to this specific embodiment of step b) of the screening method above, said step b) of assaying for the binding of said candidate substance to a L,D-transpeptidase as defined above comprises the following steps:
b1) subjecting said L,D-transpeptidase to proteolysis, so as to generate a plurality of peptide fragments;
b2) separating the peptide fragments obtained at the end of step c1); and
b3) detecting the complexes eventually formed between one or more of the peptide fragments separated at step b2) and the inhibitor candidate substance.

At step b1), any one of the proteases known in the art may be used. However, the most preferred protease consists of trypsin.

Trypsin digestion of said L,D-transpeptidase is performed according to methods well known in the art.

Typically, said purified L,D-transpeptidase in a suitable liquid buffer is subjected to trypsin digestion at 37° C. for a time period ranging from 1 h to 24 h, depending on the respective concentrations of said purified enzyme and of trypsin, respectively. Illustratively, said purified L,D-transpeptidase is present in a suitable buffer selected from the group consisting of (i) a 1% (w/v) ammonium bicarbonate buffer, a 25 mM potassium buffer and (iii) a 50 mM Tris-HCl buffer at pH 8.0. Then, the proteolysis reaction is stopped, for example by adding (i) 1% trifluoroacetic acid solution or (ii) phenylmethyl sulfonyl fluoride (PMSF) solution to the resulting proteolysis mixture.

Then, at step b2), the various peptide fragments that are generated by trypsin proteolysis are subjected to a separation step.

In certain embodiments, said separation step may consist of an electrophoresis gel separation of the peptide fragments, using conventional electropheresis conditions that are well known when performing classical Western blotting peptide separation.

In certain other embodiments, said separation step consists of a step of High Pressure Liquid Chromatograpgy (HPLC), for example using a LC-Packing® system that is disclosed in the examples herein.

Then, at step b3), detection of the complexes eventually formed between one or more of the peptide fragments separated at step b2) and the inhibitor candidate substance is performed.

In most embodiments of step b3), detection of the complexes eventually formed between one or more of the peptide fragments separated at step b2) and the inhibitor candidate substance is performed by:
b3-a) comparing (i) the peptide separation pattern from said L,D-transpeptidase in the absence of the inhibitor candidate substance with (ii) the peptide separation pattern from said L,D-transpeptidase when said inhibitor candidate substance has previously been contacted with the enzyme of interest;
b3-b) detecting differences between the two peptide separation patterns (i) and (ii), which differences, when present, are indicative of the binding of said inhibitor candidate compound to said said L,D-transpeptidase.

When step b2) consists of a conventional gel electrophoresis separation step, the differences between the two peptide separation patterns (i) and (ii) that are detected at step b3) consist of differences in the migration location on the gel of one or more peptide fragments onto which said inhibitor candidate compound is bound. Illustratively, the one or more peptides that are bound to the candidate substance generally migrate faster in the gel than the same unbound peptide(s).

When step b2) consists of an HPLC step, the differences between the two peptide separation patterns (i) and (ii) that are detected at step c3) consist of differences in the elution time of the one or more peptide fragments onto which said inhibitor candidate compound is bound.

In certain embodiments, said screening method may also comprise an additional step b4) of identification of the peptide fragment(s) onto which is bound said inhibitor candidate substance.

Usually, step b4) is performed by subjecting the peptide fragment(s) onto which is bound said inhibitor candidate substance to identification by mass spectrometry, for example by using an ion trap mass spectrometer as it is disclosed in the examples. Performing step b4) allows to identify precisely the binding location of said inhibitor candidate substance onto said L,D-transpeptidase, so as to determine, notably, if said inhibitor candidate compound binds to the active site or close to the active site of the enzyme, or conversely binds at a protein location which is distant of the active site of said enzyme. This will allow to discriminate, notably, between competitive and non-competitive candidate inhibitor substances.

Two Hybrid Screening System

Two-hybrid screening methods are performed for the screening of candidate substances that consist of candidate polypeptides.

In a preferred embodiment, of the screening method, the candidate polypeptide is fused to the LexA binding domain, the L,D-transpeptidase as defined above is fused to Gal 4 activator domain and step (b) is carried out by measuring the expression of a detectable marker gene placed under the control of a LexA regulation sequence that is responsive to the binding of a complete protein containing both the LexA binding domain and the Gal 4 activator domain. For example, the detectable marker gene placed under the control of a LexA regulation sequence can be the β-galactosidase gene or the HIS3 gene, as disclosed in the art.

In a particular embodiment of the screening method, the candidate compound consists of the expression product of a DNA insert contained in a phage vector, such as described by Parmley and Smith (1988). Specifically, random peptide libraries are used. The random DNA inserts encode for peptides of 8 to 20 amino acids in length (Oldenburg et al., 1992, Proc. Natl. Acad. Sci. USA, 85(8): 2444-2448; Valadon et al., 1996, J Mol Biol, 261: 11-22; Lucas, 1994, In: Development and Clinical Uses of Haemophilus b Conjugate; Westerink, 1995, Proc. Natl. Acad. Sci. USA, 92: 4021-4025; Felici et al., 1991, J Mol Biol, 222: 301-310). According to this particular embodiment, the recombinant phages expressing a polypeptide that specifically binds to a D-aspartate ligase or to a L,D-transpeptidase as defined above, are retained as expressing a candidate substance for use in the screening method above.

More precisely, in a first preferred embodiment of the screening method above, the screening system used in step (b) includes the use of a Two-hybrid screening assay. The yeast two-hybrid system is designed to study protein-protein interactions in vivo and relies upon the fusion of a bait protein to the DNA binding domain of the yeast Gal4 protein. This technique is described in the U.S. Pat. No. 5,667,973.

The general procedure of the two-hybrid assay is described hereafter. In an illustrative embodiment, the polynucleotide encoding the L,D-transpeptidase as defined above is fused to a polynucleotide encoding the DNA binding domain of the Gal4 protein, the fused protein being inserted in a suitable expression vector, for example pAS2 or pM3.

Then, the polynucleotide encoding the candidate polypeptide is fused to a nucleotide sequence in a second expression vector that encodes the activation domain of the Gal4 protein.

The two expression plasmids are transformed into yeast cells and the transformed yeast cells are plated on a selection culture medium which selects for expression of selectable markers on each of the expression vectors as well as GAL4 dependent expression of the HIS3 gene. Transformants capable of growing on medium lacking histidine are screened for gal4 dependent LacZ expression. Those cells which are positive in the histidine selection and the Lac Z assay denote the occurrence of an interaction between the L,D-transpeptidase as defined above and the candidate polypeptide and allow to quantify the binding of the two protein partners.

Since its original description, the yeast two-hybrid system has been used extensively to identify protein-protein interactions from many different organisms. Simultaneously, a number of variations on a theme based on the original concept have been described. The original configuration of the two-hybrid fusion proteins was modified to expand the range of possible protein-protein interactions that could be analyzed. For example, systems were developed to detect trimeric interactions. Finally, the original concept was turned upside down and 'reverse n-hybrid systems' were developed to identify peptides or small molecules that dissociate macromolecular interactions (Vidal et al., 1999, Yeast forward and reverse 'n'-hybrid systems. Nucleic Acids Res. Feb. 15, 1999; 27(4): 919-29). These variations in the two-hybrid system can be applied to the disruption of the interaction between candidates antibacterial polypeptides and a L,D-transpeptidase as defined above and enters in the scope of the present invention.

Western Blot

In another preferred embodiment, of the screening method according to the invention, step (b) consists of subjecting to a gel migration assay the mixture obtained at the end of step (a) and then measuring the binding of the candidate polypeptide with the L,D-transpeptidase as defined above by performing a detection of the complexes formed between the candidate polypeptide and said L,D-transpeptidase as defined above.

The gel migration assay can be carried out by conventional widely used western blot techniques that are well known from the one skilled in the art.

The detection of the complexes formed between the candidate polypeptide and the L,D-transpeptidase as defined above can be easily observed by determining the stain position (protein bands) corresponding to the proteins analyzed since the apparent molecular weight of a protein changes if it is in a complex.

On the one hand, the stains (protein bands) corresponding to the proteins submitted to the gel migration assay can be detected by specific antibodies for example antibodies specifically directed against the L,D-transpeptidase as defined above or against the candidate polypeptide, if the latter are available. Alternatively, the candidate polypeptide or the L,D-transpeptidase as defined above can be tagged for an easier revelation of the gel, for example by fusion to GST, HA, poly Histidine chain, or other probes in order to facilitate the identification of the different protein on the gel, according to widely known techniques.

Biosensor

In another preferred embodiment of the screening method above, the screening system used in step (b) includes the use of an optical biosensor such as described by Edwards and Leatherbarrow (1997, Analytical Biochemistry, 246: 1-6) or also by Szabo et al. (1995, Curr. Opinion Struct. Biol., 5(5): 699-705). This technique permits the detection of interactions between molecules in real time, without the need of labelled molecules. This technique is based on the surface plasmon resonance (SPR) phenomenon. Briefly, a first protein partner molecule, for example the candidate polypeptide, is attached to a surface (such as a carboxymethyl dextran matrix). Then, the second protein partner molecule, in this case the L,D-transpeptidase as defined above, is incubated with the first partner, in the presence or in the absence of the candidate compound to be tested and the binding, including the binding level, or the absence of binding between the first and second protein partner molecules is detected. For this purpose, a light beam is directed towards the side of the surface area of the substrate that does not contain the sample to be tested and is reflected by said surface. The SPR phenomenon causes a decrease in the intensity of the reflected light with a specific combination of angle and wavelength. The binding of the first and second protein partner molecules causes a change in the refraction index on the substrate surface, which change is detected as a change in the SPR signal.

According to the preferred embodiment of the screening method cited above, the "first partner" of the screening system consists of the substrate onto which the first protein partner molecule is immobilized, and the "second partner" of the screening system consists of the second partner protein molecule itself.

Affinity Chromatography

Candidate compounds for use in the screening method above can also be selected by any immunoaffinity chromatography technique using any chromatographic substrate onto which (i) the candidate polypeptide or (ii) L,D-transpeptidase as defined above, have previously been immobilized, according to techniques well known from the one skilled in the art.

In a preferred embodiment of the invention, the screening method includes the use of affinity chromatography.

The L,D-transpeptidase as defined above may be attached to a column using conventional techniques including chemical coupling to a suitable column matrix such as agarose, Affi Gel®, or other matrices familiar to those of skill in the art. In some embodiment of this method, the affinity column contains chimeric proteins in which the L,D-transpeptidase as defined above, is fused to glutathion-s-transferase (GST). Then a candidate compound is applied to the affinity column. The amount of the candidate compound retained by the immobilized L,D-transpeptidase as defined above allows measuring the binding ability of said candidate compound on the enzyme and thus allows to assess the potential antibacterial activity of said candidate compound.

High Throughput Screening

In another preferred embodiment of the screening method according to the invention, at step (b), the candidate substance and the the L,D-transpeptidase as defined above are labelled by a fluorophore. The measurement of the binding of the candidate compound to the L,D-transpeptidase as defined above, at step (b) consists of measuring a fluorescence energy transfer (FRET). Disruption of the interaction by a candidate compound is then followed by decrease or absence of fluorescence transfer. As an example, the one skilled in the art can make use of the TRACE technology of fluorescence transfer for Time Resolved Amplified Cryptate Emission developed by Leblanc V, et al. for measuring the FRET. This technique is based on the transfer of fluorescence from a donor (cryptate) to an acceptor of energy (XL665), when the two molecules are in close proximity in cell extracts.

Generally, the method for the screening of antibacterial substance that binds to a L,D-transpeptidase as defined above comprises further steps wherein the candidate substances that bind to the enzyme and which are thus positively selected at the end of step (b) of the screening method, are then assayed for their ability to actually inhibit said enzyme activity, by performing, as step (c) of said method, the corresponding screening method comprising a step of determining the ability of said candidate substances to inhibit the activity of a L,D-transpeptidase comprising a polypeptide having an amino acid sequence possessing at least 50% amino acid identity with the amino acid sequence of SEQ ID No 1, or a biologically active fragment thereof.

Compositions or Kits for the Screening of Antibacterial Substances

The present invention also relates to compositions or kits for the screening of antibacterial substances.

In certain embodiments, said compositions or kits comprise a purified L,D-transpeptidase, preferably under the form of a recombinant protein.

In said compositions or said kits, said L,D-transpeptidase may be under a solid form or in a liquid form.

Solid forms encompass powder of said L,D-transpeptidase under a lyophilized form.

Liquid forms encompass standard liquid solutions known in the art to be suitable for protein long time storage.

Preferably, said L,D-transpeptidase is contained in a container such as a bottle, e.g. a plastic or a glass container.

In certain embodiments, each container comprises an amount of said L,D-transpeptidase ranging from 1 ng to 10 mg, either in a solid or in a liquid form.

Further, said kits may comprise also one or more reagents, typically one or more substrate(s), necessary for assessing the enzyme activity of said L,D-transpeptidase.

Illustratively, if said kit comprises a container of L,D-transpeptidase, then said kit may also comprise (i) a container comprising an appropriate amount of the substrate, the disaccharide-tetrapeptide (GlcNac-MurNac-L-Ala1-D-iGln2-mesoDapNH23-D-Ala4).

In certain embodiments, a kit according to the invention comprises one or more of each of the containers described above.

Assessment of the Ex Vivo Activity of the Inhibitors Compounds Positively Selected by the In Vitro Screening Methods Disclosed Above Inhibitor substances that have been positively selected at the end of any one of the in vitro screening methods that are previously described in the present specification may then be assayed for their ex vivo antibacterial activity, in a further stage of their selection as a useful antibacterial active ingredient of a pharmaceutical composition.

By "ex vivo" antibacterial activity, it is intended herein the antibacterial activity of a positively selected candidate compound against *Mycobacterium tuberculosis* cells that are cultured in vitro.

Thus, any substance that has been shown to behave like an inhibitor of a L,D-transpeptidase, after positive selection at the end of any one of the in vitro screening methods that are disclosed previously in the present specification, may be further assayed for his ex vivo antibacterial activity against *Mycobacterium tuberculosis* cells.

Consequently, any one of the screening methods that are described above may comprise a further step of assaying the positively selected inhibitor substance for its ex vivo antibacterial activity.

Usually, said further step consists of preparing in vitro cultures of *Mycobacterium tuberculosis* and then adding to said bacterial cultures the candidate compound to be tested, before determining the ability of said candidate compound to block bacterial growth or even most preferably kill the cultured bacterial cells.

Most preferably, the candidate antibacterial compound is added to cultures of *Mycobacterium tuberculosis* that are maintained in vitro in a dormant state.

As intended herein and also as it is largely admitted in the art, *Mycobacterium tuberculosis* cells in a "dormant state" consist of these mycobacterial cells that are under a reversible state of low metabolic activity, in which cells persist for extended periods without division.

As it has already been disclosed at the beginning of the present specification, *Mycobacterium tuberculosis* cells in a dormant state are found within the body cells of an infected individual, especially in macrophages, particularly in particular environment such as granuloma or caseum.

Dormant state of *Mycobacterium cells* may be mimicked in vitro according to various methods well known in the art.

In certain embodiments, *Mycobacterium tuberculosis* cells in a dormant state may be generated in vitro by nutrient starvation, such as described by Betts et al. (2002, Mol. Microbiol., Vol. 43: 717-731) or by Hampshire et al. (2004, in Tuberculosis (Edinb), Vol. 84: 228-238).

Obtaining *Mycobacterium tuberculosis* cells in a dormant state by nutrient starvation may be performed by the illustrative method described hereafter. Seeds of *Mycobacterium tuberculosis* H37Rv (National Collection of Tissue Culture, London, UK, Ref NCTC 7416) are grown to late log phase without shaking and then diluted 1:100 into a roller bottle in 100 ml Middlebrook 7H9 media supplemented with 0.2% (v/v) glycerol, 10% (v/v) albumin-dextrose-catalase (ADC) and 0.025% (v/v) Tween® 80 at 37° C. with constant rolling at 2 r.p.m. After 7 days growth to log phase, cultures are pelleted and washed twice with PBS before being resuspended in PBS, transferred to standing flasks or microtiter plates and incubated at 37° C. For viability determination during starvation, bacteria are cultured in 10 ml volumes in 30 ml bottles, and the number of cfu ml$^{-1}$ is determined by plating serial dilutions onto 7H10 agar from triplicate cultures at several time points (day 0, weeks, 1, 2, 3 and 6). A visual indication of oxygen depletion may be gained by the addition of sterile methyene blue solution (500 μg ml$^{-1}$) to a final concentration of 1.5 μg ml$^{-1}$ to 10 ml standing cultures maintained under starvation conditions or in Middlebrook 7H9 supplemented as above. Control flasks containing either PBS or Middlebrook 7H9 medium and methylene blue but no bacteria may also be set up.

In other embodiments, *Mycobacterium tuberculosis* cells in a dormant state may be generated in vitro by oxygen deprivation, such as described by Wayne et al. (1996, Infect. Immun., Vol. 64: 2062-2069).

In still other embodiments, *Mycobacterium tuberculosis* cells in a dormant state may be generated in vitro by exposure to nitric oxide, such as described by Voskuil et al. (2003, J. Exp. Med., Vol. 198: 705-713).

Typically, bacterial cells, most preferably in a dormant state, are plated in Petri dishes containing the appropriate culture medium, generally in agar gel, at a cell number ranging from 10 to $10^3$ bacterial cells, including from 10 to $10^2$ bacterial cells. In certain embodiments, serials of bacterial cultures are prepared with increasing numbers of seeded bacterial cells.

Typically, the candidate compound to be tested is then added to the bacterial cultures, preferably with a serial of amounts of said candidate compounds for each series of a given plated cell number of bacterial cultures.

Then, the bacterial cultures are incubated in the appropriate culture conditions, most preferably starvation conditions, for instance in a cell incubator at the appropriate temperature, and for an appropriate time period, for instance a culture time period ranging from 1 day to 4 days, before counting the resulting CFUs (Colony Forming Units), either manually under a light microscope or binocular lenses, or atomically using an appropriate apparatus.

Generally, appropriate control cultures are simultaneously performed, i.e; negative control cultures without the candidate substance and positive control cultures with an antibiotic that is known to be toxic against the cultured bacterial cells.

Finally, said candidate compound is positively selected at the end of the method if it reduces the number of CFUs, as compared with the number of CFUs found in the corresponding negative control cultures.

Thus, another object of the present invention consists of a method for the ex vivo screening of a candidate antibacterial substance which comprises the steps of:

a) performing a method for the in vitro screening of a antibacterial substances as disclosed in the present specification, with a candidate substance; and b) assaying a candidate substance that has been positively selected at the end of step a) for its ex vivo antibacterial activity.

Assessment of the in vivo Activity of the Inhibitor Compounds Positively Selected by the in vitro or ex vivo Screening Methods Disclosed Above Inhibitor substances that have been positively selected at the end of any one of the screening methods that are previously described in the present specification may then be assayed for their in vivo antibacterial activity, in a further stage of their selection as a useful antibacterial active ingredient of a pharmaceutical composition.

Thus, any substance that has been shown to behave like an inhibitor of a L,D-transpeptidase, after positive selection at the end of any one of the screening methods that are disclosed previously in the present specification, may be further assayed for his in vivo antibacterial activity.

Consequently, any one of the screening methods that are described above may comprise a further step of assaying the positively selected inhibitor substance for its in vivo antibacterial activity.

Usually, said further step consists of administering the inhibitor substance to a mammal and then determining the antibacterial activity of said substance.

Mammals are preferably non human mammals, at least at the early stages of the assessment of the in vivo antibacterial effect of the inhibitor compound tested. However, at further stages, human volunteers may be administered with said inhibitor compound to confirm safety and pharmaceutical activity data previously obtained from non human mammals.

Non human mammals encompass rodents like mice, rats, rabbits, hamsters, guinea pigs. Non human mammals and also cats, dogs, pigs, veals, cows, sheep, goats. Non human mammals also encompass primates like macaques and baboons.

Thus, another object of the present invention consists of a method for the in vivo screening of a candidate antibacterial substance which comprises the steps of:

a) performing a method for the in vitro screening of a antibacterial substances as disclosed in the present specification, with a candidate substance; and b) assaying a candidate substance that has been positively selected at the end of step a) for its in vivo antibacterial activity.

Preferably, serial of doses containing increasing amounts of the inhibitor substance are prepared in view of determining the antibacterial effective dose of said inhibitor substance in a mammal subjected to a bacterial infection. Generally, the $ED_{50}$ dose is determined, which is the amount of the inhibitor substance that is effective against *Mycobacterium tuberculosis* in 50% of the animals tested. In some embodiments, the $ED_{50}$ value is determined for various distinct bacteria species, in order to assess the spectrum of the antibacterial activity.

In certain embodiments, it is made use of serial of doses of the inhibitor substance tested ranging from 1 ng to 10 mg per kilogram of body weight of the mammal that is administered therewith.

Several doses may comprise high amounts of said inhibitor substance, so as to assay for eventual toxic or lethal effects of said inhibitor substance and then determine the $LD_{50}$ value, which is the amount of said inhibitor substance that is lethal for 50% of the mammal that has been administered therewith.

The inhibitor substance to be assayed may be used alone under the form of a solid or a liquid composition.

When the inhibitor substance is used alone, the solid composition is usually a particulate composition of said inhibitor substance, under the form of a powder.

When the inhibitor substance is used alone, the liquid composition is usually a physiologically compatible saline buffer, like Ringer's solution or Hank's solution, in which said inhibitor substance is dissolved or suspended.

In other embodiments, said inhibitor substance is combined with one or more pharmaceutically acceptable excipients for preparing a pre-pharmaceutical composition that is further administered to a mammal for carrying out the in vivo assay.

Before in vivo administration to a mammal, the inhibitor substances selected through any one of the in vitro screening methods above may be formulated under the form of pre-pharmaceutical compositions. The pre-pharmaceutical compositions can include, depending on the formulation desired, pharmaceutically acceptable, usually sterile, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the test composition or formulation may also include other carriers, adjuvants, or non-toxic, non-therapeutic, non-immunogenic stabilizers and the like.

Compositions comprising such carriers can be formulated by well known conventional methods. These test compositions can be administered to the mammal at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by taking into account, notably, clinical factors. As is well known in the medical arts, dosages for any one mammal depends upon many factors, including the mammal's size, body surface area, age, the particular compound to be administered, sex, time and route of administration and general health. Administration of the suitable pre-pharmaceutical compositions may be effected by different ways, e.g., by intravenous, intraperitoneal, subcutaneous, intramuscular, topical or intradermal administration. If the regimen is a continuous infusion, it should also be in the range of 1 ng to 10 mg units per kilogram of body weight per minute, respectively. Progress can be monitored by periodic assessment. The pre-pharmaceutical compositions of the invention may be administered locally or systemically. Administration will generally be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, anti-oxidants, chelating agents, and inert gases and the like.

The inhibitor substances may be employed in powder or crystalline form, in liquid solution, or in suspension.

The injectable pre-pharmaceutical compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline, or another injectable liquid, e.g., peanut oil for intramuscular injections. Also, various buffering agents, preservatives and the like can be included.

Topical applications may be formulated in carriers such as hydrophobic or hydrophilic base formulations to provide ointments, creams, lotions, in aqueous, oleaginous, or alcoholic liquids to form paints or in dry diluents to form powders.

Oral pre-pharmaceutical compositions may take such forms as tablets, capsules, oral suspensions and oral solutions. The oral compositions may utilize carriers such as conventional formulating agents and may include sustained release properties as well as rapid delivery forms.

In certain embodiments of the in vivo screening assay, the inhibitor substance is administered to a mammal which is the subject of a bacterial infection. For non human mammals, these animals have been injected with a composition containing bacteria prior to any administration of the inhibitor compound.

In certain other embodiments of the in vivo screening assay, non human animals are administered with the inhibitor compound to be tested prior to being injected with a composition containing bacteria.

Generally, non human mammals are injected with a number of *Mycobacterium tuberculosis* cells ranging from $1 \times 10^2$ to $1 \times 10^{12}$ cells, including from $1 \times 10^6$ to $1 \times 10^9$ cells. In some embodiments, *Mycobacterium tuberculosis* cells in an in vitro-generated dormant state are used for injection.

Generally, bacteria cells that are injected to the non human mammals are contained in a physiologically acceptable liquid solution, usually a saline solution like Ringer's solution or Hank's solution.

Generally, in the embodiment wherein the inhibitor compound to be tested is administered subsequently to bacterial inoculation, said inhibitor compound is administered form 1 hour to 96 hours after bacterial injection, including from 6 hours to 48 hours after bacterial injection.

Generally, in the embodiment wherein the inhibitor compound to be tested is administered prior to bacterial injection, said inhibitor compound is administered from 1 min to 3 hours prior to bacterial injection.

Generally, all animals are sacrificed at the end of the in vivo assay.

For determining the in vivo antibacterial activity of the inhibitor compound that is tested, blood or tissue samples of the tested animals are collected at determined time periods after administration of said inhibitor compound and bacteria counts are performed, using standard techniques, such as staining fixed slices of the collected tissue samples or plating the collected blood samples and counting the bacterial colonies formed.

Then, the values of the bacteria counts found for animals having been administered with increasing amounts of the inhibitor compound tested are compared with the value(s) of bacteria count(s) obtained from animals that have been injected with the same number of bacteria cells but which have not been administered with said inhibitor compound.

As already disclosed earlier in the present specification, various carbapenem candidate compounds have been assayed with the screening method of the invention and have been positively selected as compounds having a great potential value for treating individuals who have been infected by *Mycobacterium tuberculosis* and who have entered the asymptomatic phase of the disease, which may also be termed "latent tuberculosis", wherein numerous *Mycobacterium tuberculosis* cells in a dormant state are found in the organ cells, including into macrophage cells, which latent tuberculosis state may diagnosed by performing the well known skin test of Mantoux consisting of an intradermal injection of a suspension of purified protein derivative (PPD) containing tuberculin, generally into the volar surface of the forearm and measure the diameter of skin induration after from about 48 hours to about 72 hours following injection.

Thus, it has been found according to the invention that carbapenem compounds, that have been already tested in the art in individuals who were infected with multi-drug-resistant (MDR) strains of *Mycobacterium tuberculosis* and who were undergoing the clinical state of tuberculosis, may also be used for treating tuberculosis patients in the latent phase, i.e. asymptomatic phase, of the disease. For an exhaustive review of the clinical definition of the tuberculosis latent phase, the one skilled in the art may refer to the standard data published by the National Institute for Health and Clinical Excellence (NICE, London, UK)

Consequently, another object of the present invention consists of the use of carbapenem compounds for treating individuals having latent tuberculosis.

This invention thus relates to the use of a carbapenem compound for manufacturing a pharmaceutical composition for treating individuals having latent tuberculosis.

This invention also pertains to a method for treating individuals having latent tuberculosis comprising a step of administering to the said individuals an effective amount of one or more carbapenem compounds.

By "carbapenem", it is intended herein any compound belonging to the beta-lactam antibiotics and possessing in their structural formula the backbone structure of the following formula (I):

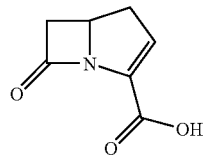

(I)

Carbapenem compounds include imipenem, meropenem, ertapenem, faropenem, doripenem and panipenem.

This invention also relates to pharmaceutical composition comprising one or more carbapenem compounds for the purpose of treating individuals having latent tuberculosis. Preferably, in such a pharmaceutical composition, the said one or more carbapenem compound(s) is (are) combined with one or more pharmaceutically acceptable excipient(s).

Such pharmaceutical compositions are under the form of dosage forms adapted for a daily administration of an amount of carbapenem of at least 1 mg and up to 10 g, Such pharmaceutical compositions are preferably adapted for a daily administration of at least 10 mg, 50 mg, 100 mg, 200 mg, 300 mg, 400 mg, 500 mg, 600 mg, 700 mg, 800 mg or 900 mg.

Such pharmaceutical compositions are preferably adapted for a daily administration of up to 1 g, 2 g, 3 g or 4 g.

The effective amount of carbapenem may be easily adapted by the one skilled in the art, depending notably on the age and of the weight individual to be treated.

The daily amount of carbapenem may be administered to the patient through one or more uptakes, e.g. from one to six uptakes.

Illustratively, the daily amount of imipenem to be administered to an adult patient weighing 80 kg will typically ranges from 1 g to 4 g.

Illustratively, the daily amount of meropenem, ertapenem, faropenem, doripenem or panipenem to be administered to an adult patient weighing 80 kg will typically be of about 1 g.

Generally, the pharmaceutical compositions comprising carbapenem which are used according to the invention are under the form of a powder for preparing injectable liquid solutions.

Generally, the injectable pharmaceutical compositions comprising carbapenem are administered by a parenteral route, including intravenous route.

Other possible features of the pharmaceutical compositions comprising carbapenem that may be used according to the invention, as well as of the methods of treatment may be found above where pharmaceutical uses of the L,D-transpeptidase inhibitors that have been selected positively by the screening methods are described.

This invention is further illustrated by, without in any way being limited to, the examples herein.

EXAMPLES

A. Materials and Methods of the Examples

A.1. Growth Conditions, Purification and Peptidoglycan Structure Analysis Peptidoglycan.

M. tuberculosis H37Rv was grown at 37° C. without shaking in Dubos broth (Difco) supplemented with 10% (vol/vol) of OADC medium (Becton Dickinson), which contains oleic acid, BSA fraction V-glucose, and catalase. A 10-day preculture of 25 ml was used to inoculate 250 ml of the growth medium. After 3 weeks of incubation, bacteria were collected by centrifugation, resuspended in 25 ml of 10 mM phosphate buffer (pH 7.0), and inactivated by heat (96° C. for 30 min). A second inactivation step was performed by adding 8% SDS (vol/vol) followed by an incubation of 30 min at 96° C. Bacteria were collected by centrifugation and disrupted with glass beads (150-212 μm; 5 g/5 ml, weight/vol) for 16 h at 4° C. in a cell disintegrator (The Mickle Laboratory Engineering Co, Gromshall, United Kingdom). The peptidoglycan was collected by centrifugation (15,000×g for 15 min at 4° C.), extracted with 8% boiling SDS, and washed three times with water. Peptidoglycan was treated with proteases, digested with mutanolysin and lysozyme, as previously described for purification of the peptidoglycan from enterococci (Arbeloa et al., 2007, J. Biol. Chem., Vol. 279: 41546-41556). The resulting muropeptides were treated with ammonium hydroxide to cleave the ether link internal to MurNAc (Arbeloa et al., 2007, Supra) or with sodium borohydride to reduce MurNAc into muramitol (Mainardi et al., 2000, J. Biol. Chem., Vol. 275: 16490-16496). Peptidoglycan fragments were purified by rp-HPLC and analyzed by mass spectrometry (Arbeloa et al., 2007, Supra).

A.2. Production and Purification of Recombinant $Ldt_{Mt1}$.

A portion of the $ldt_{Mt1}$ gene, previously designated Rv0116C (http://www.ncbi.nlm.nih.gov/), was amplified with primers 5'-TTCCATGGCGCCACTCCAACCGATCC-3' (SEQ ID No 3) and 5'-TTGGATCCGCCGACCACCTCAATGGGA-3' (SEQ ID No 4). The PCR product was digested with NcoI plus BamHI (underlined) and cloned into pET2818 (18). The resulting plasmid encoded a fusion protein consisting of a methionine specified by the ATG initiation codon of pET2818, residues 32 to 251 of $Ldt_{Mt1}$, and a C-terminal polyhistidine tag with the sequence $GSH_6$. E. coli BL21 (DE3) harboring pREP4GroESL (Amrein et al., 1995, Proc. Natl. Acad. Sci USA, Vol. 92: 1048-1052) and pET2818☐$ldt_{Mt1}$ was grown at 37° C. to an $OD_{600}$ of 0.6 in three liters of brain heart infusion broth containing ampicillin (150 μg/ml). Isopropyl-D-thiogalactopyranoside was added to a final concentration of 0.5 mM and incubation was continued for 17 h at 16° C. $Ldt_{Mt1}$ was purified from a clarified lysate by affinity chromatography on $Ni^{2+}$-nitrilotriacetate-agarose resin (Qiagen GmbH, Hilden, Germany) followed by anion exchange chromatography (MonoQ HR5/5, Amersham Pharmacia Biotech) with a NaCl gradient in 50 mM Tris-HCl pH 8.5. An additional size exclusion chromatography was performed on a Superdex HR10/30 column (Amersham Pharmacia Biotech) equilibrated with 50 mM Tris-HCl (pH 7.5) containing 300 mM NaCl at a flow rate of 0.5 ml/min. The protein was concentrated by ultrafiltration (Amicon Ultra-4 centrifugal filter devices, Millipore) and stored at −20° C. in the same buffer supplemented with 20% glycerol.

A.3. L,D-Transpeptidase Assays.

The disaccharide-tetrapeptide containing amidated meso-diaminopimelic acid (GlcNAc-MurNAc-L-Ala$^1$-D-iGln$^2$-mesoDap$_{NH2}^3$-D-Ala$^4$) was purified from *C. jeikeium* strain CIP103337 and the concentration w as determined by amino acid analysis after acid hydrolysis (Arbeloa et al., 2007, J. Biol. Chem., Vol. 279: 41546-41556; Auger et al., FEMS Microbiol. Lett., Vol. 219: 115-119). In vitro formation of muropeptide dimers was tested in 10 µL of 50 mM Tris-HCl (pH 7.5) containing 300 mM NaCl, 11 µM Ldt$_{Mt1}$, and 280 µM disaccharide-tetrapeptide. The reaction mixture was incubated for 2 hours at 37° C., treated with ammonium hydroxide, and the resulting lactoyl-peptides were analyzed by nanoelectrospray tandem mass spectrometry using N$_2$ as the collision gas (Arbeloa et al., 2007, Supra).

A.4. Inhibition of Ldt$_{Mt1}$ by β-Lactams.

Ldt$_{Mt1}$ (12.5 µM) was pre-incubated for 20 min at 37° C. with ampicillin (Bristol-Myers), ceftriaxone (Roche Applied Science), and imipenem (Merck Sharpe and Dhome-Chibret) in 50 mM Tris-HCl (pH 7.5) containing 300 mM NaCl (buffer A). The L,D-transpeptidation reaction was started by the addition of the disaccharide-tetrapeptide (final concentration 280 µM) and allowed to proceed for 2 hours at 37° C. The reaction products were detected by mass spectrometry (Mainardi et al., 2007, J. Biol. Chem., Vol. 282: 30414-30422).

The formation of enzyme-drug adducts was tested by incubating Ldt$_{Mt1}$ (12.5 µM) with β-lactams (125 µM) for 1 h at 37° C. in buffer A. The reaction mixture was dialyzed against water for 30 min and the average mass of proteins and protein-β-lactam adducts was determined as described (Mainardi et al., 2007, Supra).

B. Results of the Examples

Example 1

Figure 2A:
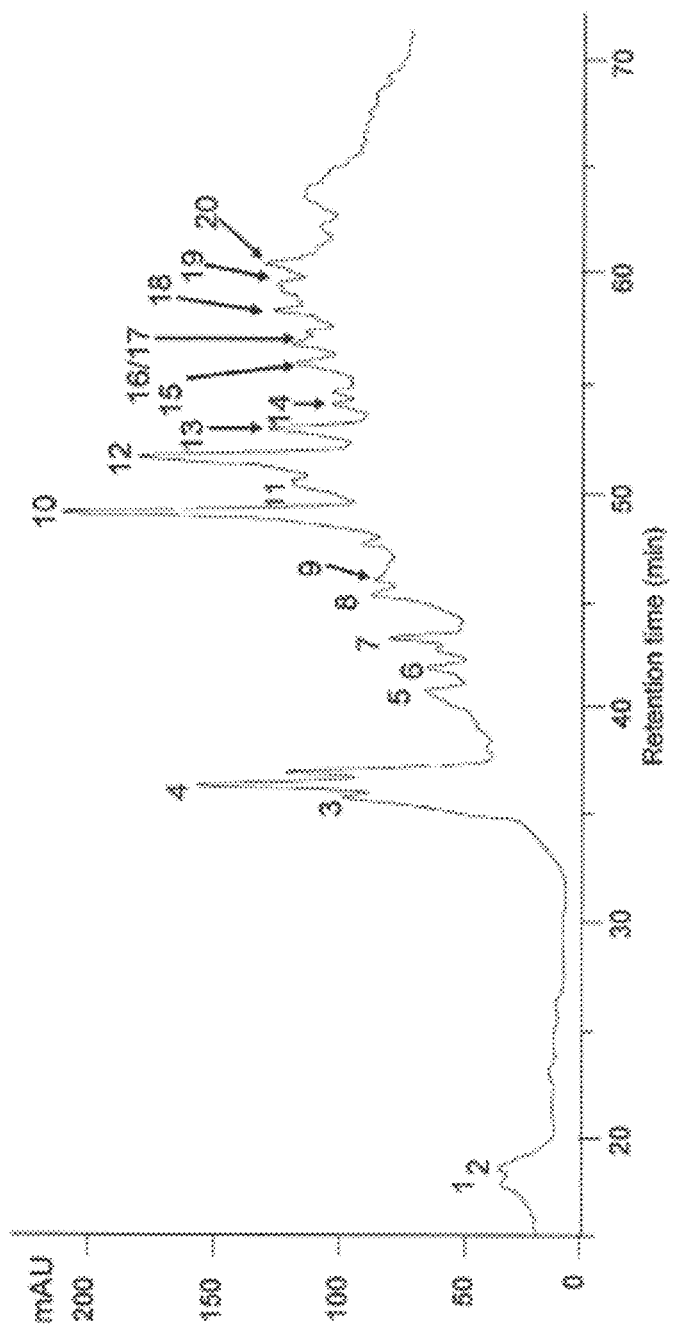
Figure 2:
Figure 2:
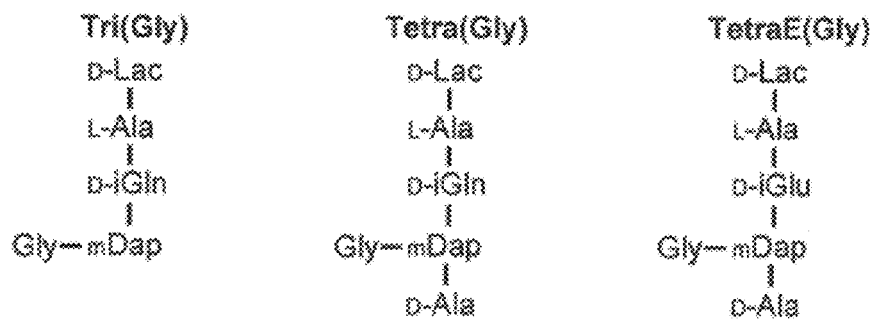
Figure 2C:
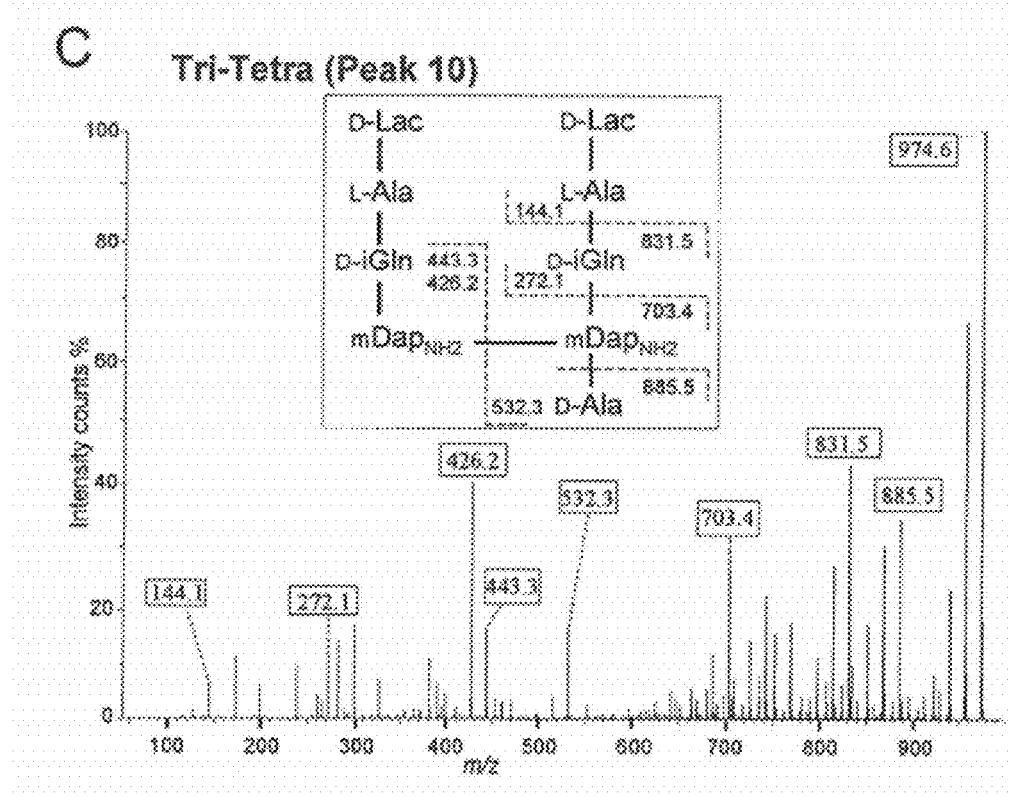
Figure 2D:
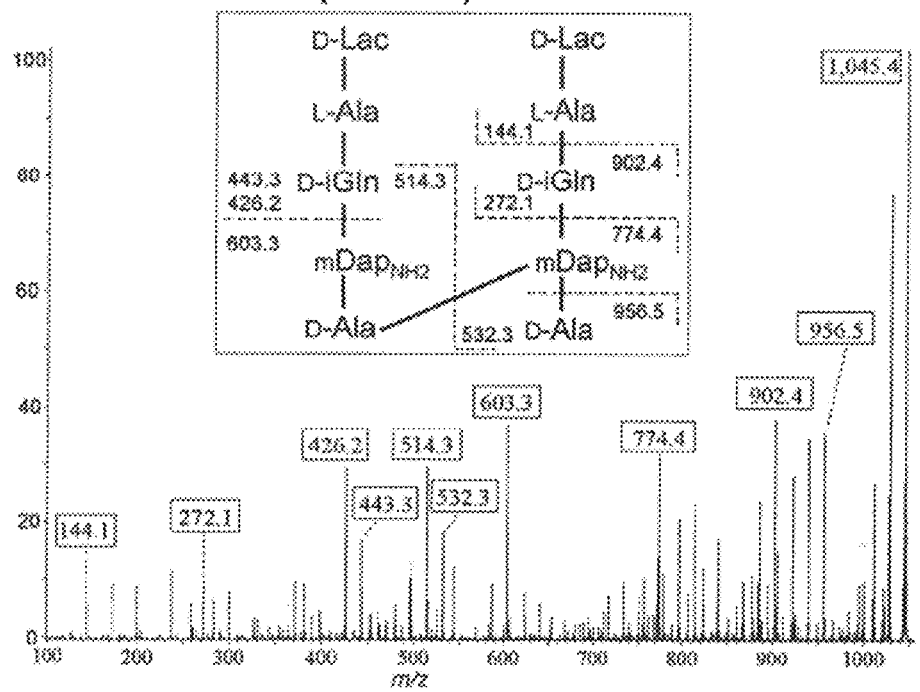

Cross-Links Generated by L,D-Transpeptidation are Predominant in the Peptidoglycan from *M. tuberculosis* in Stationary Phase after Growth in Rich Medium The peptidoglycan of *M. tuberculosis* H37Rv was analyzed by reverse phase-high performance liquid chromatography (rp-HPLC) (FIG. 2A) and mass spectrometry (FIG. 2B and Table 1 hereunder) to evaluate the contribution of D,D- and L,D-transpeptidases to the formation of cross-links. Peptidoglycan dimers contained both mDap$^3$→mDap$^3$ cross-links generated by L,D-transpeptidation (FIG. 2C) and D-Ala$^4$→mDap$^3$ cross-links generated by D,D-transpeptidation (FIG. 2D). A comprehensive analysis of the dimers indicated that the majority (80%) of the cross-links were generated by L,D-transpeptidation. Such a high content in 3→3 cross-links has never been reported in wild-type isolates of eubacteria revealing that the L,D-transpeptidation reaction is likely to have an essential role in the adaptation of *M. tuberculosis* to the stationary phase.

High resolution mass-spectrometry analysis of the peptidoglycan of *M. tuberculosis* H37Rv confirmed several features previously identified in disaccharide-peptide monomers. The stem peptide contained L-Ala at the 1$^{st}$ position and predominantly D-iGln at the 2$^{nd}$ position, which was occupied to a lesser extent by D-iGlu due to the absence of amidation of the α-carboxylate (FIG. 2B and Table 1 hereunder). Likewise, the ε-carboxylate of mDap at the 3$^{rd}$ position was mostly amidated. Gly residues linked to the ε-amine of mDap were also detected and formed cross-bridges in muropeptide dimers. Presence of Gly has been previously reported in the peptidoglycan of *M. tuberculosis* but the position of this residue was not determined. D-Ala, mostly present at the 4$^{th}$ position, was replaced by Asn, presumably of the D configuration, in a minority of the stem peptides. Since the latter amino acid was abundant in the culture medium, its presence in muropeptides could result from the exchange of D-Ala with D-Asn in the peptidoglycan due to an L,D-transpeptidation reaction.

In order to analyze the sugar moiety of muropeptides, peptidoglycan fragments were reduced with sodium borohydride in place of the ammonium hydroxide treatment. This analysis confirmed the presence of N-glycolylmuramic acid (MurNGlyc) or N-acetylmuramic acid (MurNAc) linked to N-acetylglucosamine or glucosamine. Anhydro forms of disaccharide-peptides were also detected, indicative of the terminal unit of the glycan chains. These forms were not modified by treatment with ammonium hydroxide (Table 1 hereunder).

Table 1: Peptidoglycan Composition

TABLE 1

| Peak | Muropeptide | Cross-link | Mass$^a$ | (%) |
|---|---|---|---|---|
| Monomers | | | | |
| 1 | Tri | NA | 460.2 | 2.8 |
| 2 | Tri-Asn | NA | 574.3 | 2.5 |
| 3 | Tri(Gly) | NA | 518.2 | 6.5 |
| 4 | Tetra | NA | 531.3 | 13.0 |
| 5 | Tetra(Gly) | NA | 589.3 | 5.3 |
| 6 | TetraE(Gly) | NA | 590.3 | 2.3 |
| 14 | Tetra(anh) | NA | 935.4 | 1.9 |
| Dimers | | | | |
| 7 | Tri-Tri | 3-3 | 902.5 | 4.9 |
| 8 | Tri-Tri-Asn | 3-3 | 1,016.5 | 4.2 |
| 9 | Tetra-Tri-Asn | 4-3 | 1,087.6 | 3.5 |
| 10 | Tri-Tetra | 3-3 | 973.5 | 14.2 |
| 11 | Tri(Gly)-TriE(Gly) | 3-3 | 1,019.5 | 4.5 |
| 12 | TriE(Gly)-TriE(Gly) | 3-3 | 1,020.5 | 12.6 |
| 13 | Tetra-Tetra | 4-3 | 1,044.5 | 5.3 |
| 15 | Tri(Gly)-TetraE(Gly) | 3-3 | 1,090.5 | 4.0 |
| 17 | TriE(Gly)-TetraE(Gly) | 3-3 | 1,091.5 | 1.2 |
| 19 | Tetra(Gly)-TetraE(Gly) | 4-3 | 1,161.6 | 1.6 |
| 20 | Tri-Tetra(anh) | 3-3 | 1,377.7 | 3.9 |
| Trimers | | | | |
| 16 | Tri-Tri-Tetra | ND | 1,415.7 | 2.9 |
| 18 | Tri-Tetra-Tetra | ND | 1,486.8 | 2.9 |

In Table 1 above, the relative abundance (%) was calculated by integration of the absorbance. aMass, observed monoisotopic mass. NA: not applicable; ND: not determined. E: D-iGlu

Example 2

Ldt$_{Mt1}$ Catalyzes Formation of 3→3 Peptidoglycan Cross-Links In Vitro

Figure 3A:
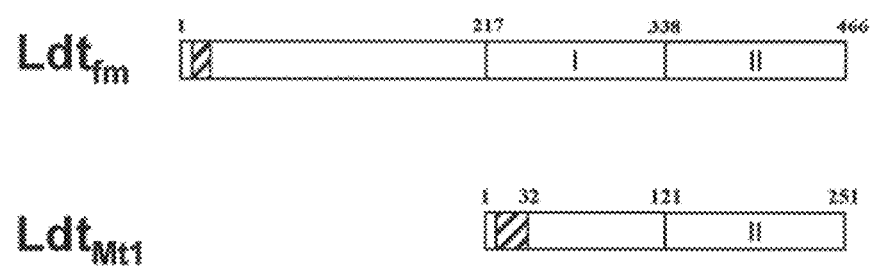
Figure 3B:
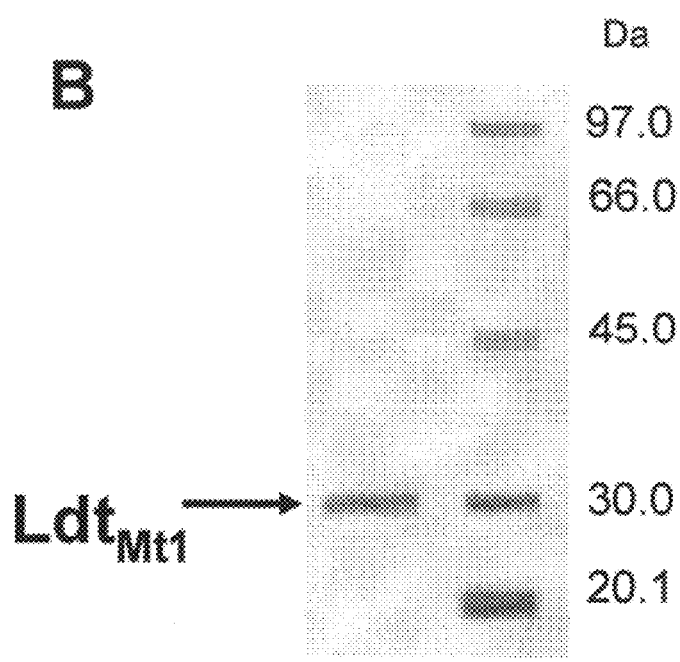
Figure 3C:
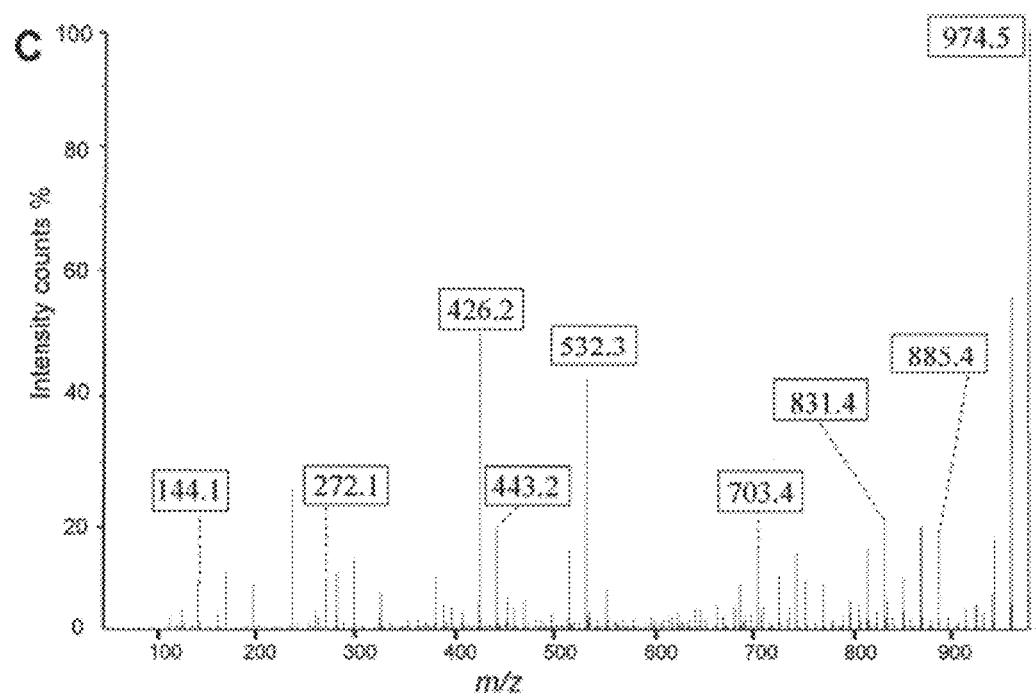
Figure 3D:
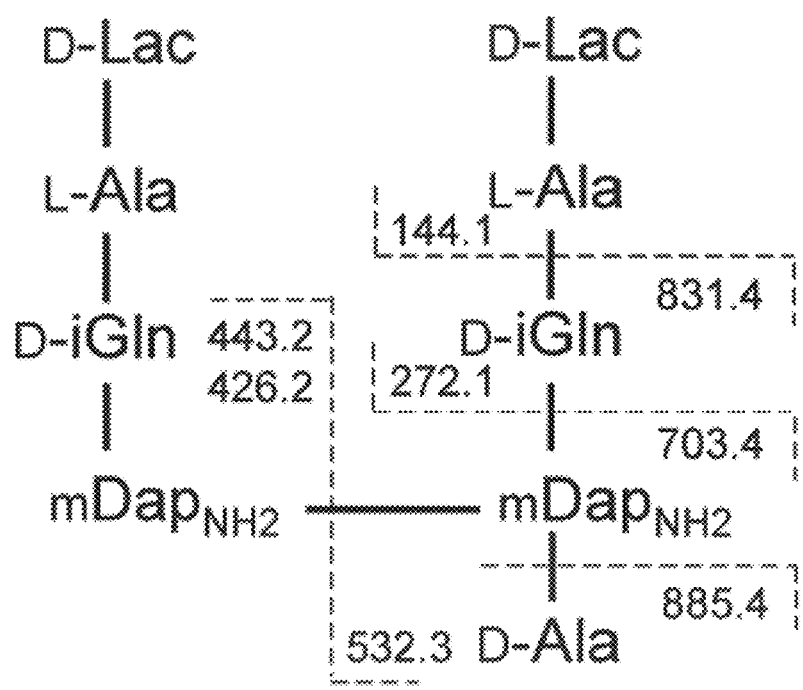

A soluble fragment of Ldt$_{Mt1}$ was produced in *E. coli*, purified (FIG. 3A and 3B), and tested for in vitro cross-linking activity using as the substrate the disaccharide-tetrapeptide monomer isolated from the peptidoglycan of *Corynebacterium jeikeium*, which has the same structure as the predominant monomer of *M. tuberculosis* (unpublished data). The products of the reaction were treated with ammonium hydroxide to cleave the ether link internal to MurNAc and the resulting lactoyl-peptides were sequenced by tandem mass spectrometry. The fragmentation pattern (FIGS. 3C and 3D) demonstrated the in vitro formation of mDap$^3$→mDap$^3$ cross-links by Ldt$_{Mt1}$. Formation of dimers was not observed with disaccharide-pentapeptide ending in D-Ala-D-Ala indicating that Ldt$_{Mt1}$ catalyzes peptidoglycan cross-linking exclusively with tetrapeptide-containing donors.

Example 3

Inactivation of Ldt$_{Mt1}$ by Formation of Adducts with β-Lactams

To investigate inhibition of the L,D-transpeptidase activity of Ldt$_{Mt1}$ by β-lactams, the formation of dimers containing mDap$^3$→mDap$^3$ cross-links was tested in the presence of various drug concentrations.

Ldt$_{Mt1}$ was not inhibited by ampicillin up to the highest tested concentration of 5.7 mM. The third-generation cephalosporin ceftriaxone was active against Ldt$_{Mt1}$ although a high drug concentration (360 μM) was required for full inhibition of enzyme activity. In contrast, the carbapenem imipenem abolished formation of mDap$^3$→mDap$^3$ cross-links at a drug to enzyme molar ratio of five.

Figure 4:
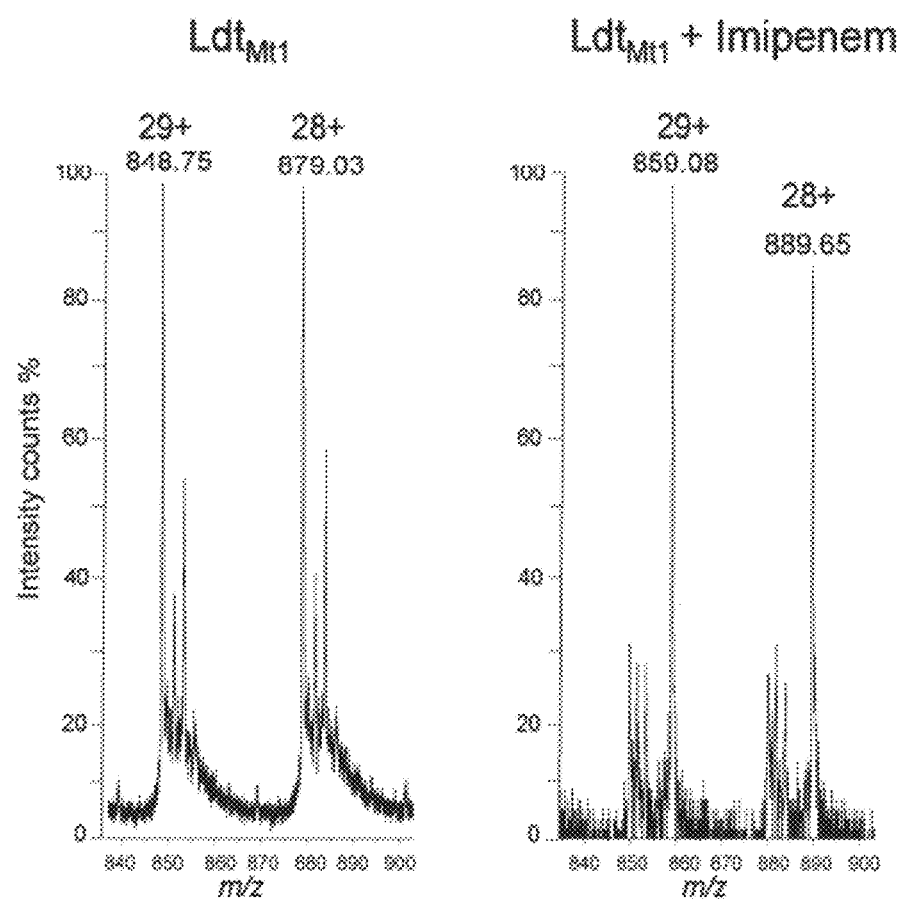

To gain insight into the mechanism of Ldt$_{Mt1}$ inhibition by β-lactams, binding of the drugs to the enzyme was tested by electrospray mass spectrometry. Incubation of Ldt$_{Mt1}$ with imipenem resulted in the formation of an adduct with an average mass matching the addition of imipenem (FIG. 4A and Table 2 hereunder). Adducts matching increments of the average mass of other carbapenems, meropenem and ertapenem, were also detected (Table 2 hereunder). No adduct was detected for ampicillin and ceftriaxone.

Table 2 Formation of Adducts Between LdtMt1 and Various β-Lactams

TABLE 2

| Beta-lactams | Average mass | |
|---|---|---|
| (average mass) | Calculated | Observed |
| None (NA) | 24,584.4 | 24,584.4 |
| Imipenem (299.4) | 24,883.7 | 24,883.5 |
| Meropenem (383.5) | 24,967.9 | 24,967.8 |
| Ertapenem (475.5) | 25,059.9 | 25,059.9 |
| Ampicillin (349.4) | 24,933.8 | ND |
| Ceftriaxone (554.6) | 25,139.0 | ND |

NA, not applicable;
ND: not detected

What is claimed is:

1. A method for killing dormant *Mycobacterium tuberculosis* cells in the treatment of individuals affected with latent tuberculosis comprising a step of administering an effective amount of one or more carbapenem compounds to the said individuals.

2. The method according to claim 1, wherein the said one or more carbapenem compounds is (are) combined with one or more pharmaceutically acceptable excipient(s) in a pharmaceutical composition.

3. The method according to claim 1, wherein the said carbapenem compound has in its structural formula the backbone structure of formula (I) below:

(I)

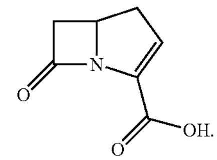

4. The method according to claim 1, wherein the said carbapenem compound is selected from the group consisting of imipenem, meropenem, ertapenem, faropenem, doripenem and panipenem.

* * * * *

SEQUENCE LISTING

<160> NUMBER OF SEQ ID NOS: 4

<210> SEQ ID NO 1
<211> LENGTH: 251
<212> TYPE: PRT
<213> ORGANISM: Mycobacterium tuberculosis

<400> SEQUENCE: 1

Met Arg Arg Val Val Arg Tyr Leu Ser Val Val Val Ala Ile Thr Leu
1               5                   10                  15

Met Leu Thr Ala Glu Ser Val Ser Ile Ala Thr Ala Ala Val Pro Pro
            20                  25                  30

Leu Gln Pro Ile Pro Gly Val Ala Ser Val Ser Pro Ala Asn Gly Ala
        35                  40                  45

Val Val Gly Val Ala His Pro Val Val Val Thr Phe Thr Thr Pro Val
    50                  55                  60

Thr Asp Arg Arg Ala Val Glu Arg Ser Ile Arg Ile Ser Thr Pro His
65                  70                  75                  80

Asn Thr Thr Gly His Phe Glu Trp Val Ala Ser Asn Val Val Arg Trp
                85                  90                  95

Val Pro His Arg Tyr Trp Pro Pro His Thr Arg Val Ser Val Gly Val
            100                 105                 110

Gln Glu Leu Thr Glu Gly Phe Glu Thr Gly Asp Ala Leu Ile Gly Val
        115                 120                 125

Ala Ser Ile Ser Ala His Thr Phe Thr Val Ser Arg Asn Gly Glu Val
    130                 135                 140

Leu Arg Thr Met Pro Ala Ser Leu Gly Lys Pro Ser Arg Pro Thr Pro
145                 150                 155                 160

Ile Gly Ser Phe His Ala Met Ser Lys Glu Arg Thr Val Val Met Asp
                165                 170                 175

Ser Arg Thr Ile Gly Ile Pro Leu Asn Ser Ser Asp Gly Tyr Leu Leu

```
              180                 185                 190
Thr Ala His Tyr Ala Val Arg Val Thr Trp Ser Gly Val Tyr Val His
        195                 200                 205

Ser Ala Pro Trp Ser Val Asn Ser Gln Gly Tyr Ala Asn Val Ser His
        210                 215                 220

Gly Cys Ile Asn Leu Ser Pro Asp Asn Ala Ala Trp Tyr Phe Asp Ala
225                 230                 235                 240

Val Thr Val Gly Asp Pro Ile Glu Val Val Gly
                245                 250

<210> SEQ ID NO 2
<211> LENGTH: 756
<212> TYPE: DNA
<213> ORGANISM: Mycobacterium tuberculosis

<400> SEQUENCE: 2
atgcgtcgag tggttcgtta tctatccgtt gtggtcgcga tcacgctgat gctcaccgcg      60
gaatcagtca gcatagcgac cgccgcggtc ccgccactcc aaccgatccc aggcgttgcg     120
tcggtgtcgc cggctaatgg tgccgtggtg ggggtggcgc accccggtggt ggtgacattc     180 accacgcccg tgaccgatcg ccgcgccgtc gagcggtcca tccgcatcag cacaccgcac     240
aacacgaccg gacacttcga gtgggtcgct agcaatgtcg tgcggtgggt gccccaccgg     300
tattggccac ctcacacccg tgtctcggtg ggtgtgcagg aactgaccga aggattcgag     360
accggtgacg cactgatcgg ggttgccagc atctcggcac ataccttcac ggtcagcaga     420
aacggagaag tcctccgcac catgcccgcg tcgttaggca agcccagccg cccgacacca     480
atcggtagct ttcacgcaat gtccaaggag cgcacggtcg tgatggactc gcgtaccatc     540
ggcatcccgc tgaattcctc ggacgggtat ctgctcaccg cccactacgc ggttcgtgtt     600
acctggagcg gcgtgtacgt gcactcggcc ccctggtcgg tcaactcgca gggatacgcc     660
aacgtcagcc acggctgtat caacctcagc ccggacaacg cggcatggta cttcgacgcc     720
gtcaccgttg gtgatcccat tgaggtggtc ggctag                               756

<210> SEQ ID NO 3
<211> LENGTH: 26
<212> TYPE: DNA
<213> ORGANISM: Artificial sequence
<220> FEATURE:
<223> OTHER INFORMATION: Synthetic primer

<400> SEQUENCE: 3
ttccatggcg ccactccaac cgatcc                                           26

<210> SEQ ID NO 4
<211> LENGTH: 27
<212> TYPE: DNA
<213> ORGANISM: Artificial sequence
<220> FEATURE:
<223> OTHER INFORMATION: Synthetic primer

<400> SEQUENCE: 4
ttggatccgc cgaccacctc aatggga                                          27
```